United States Patent
Wagner et al.

[11] Patent Number: 5,928,167
[45] Date of Patent: Jul. 27, 1999

[54] BLOOD TEST FOR ASSESSING HEPATIC FUNCTION

[75] Inventors: David A. Wagner, Nashua, N.H.; Graham M. Woolf, Los Angeles, Calif.

[73] Assignee: Metabolic Solutions, Inc., Merrimack, N.H.

[21] Appl. No.: 08/953,893

[22] Filed: Oct. 20, 1997

[51] Int. Cl.[6] .................................................. A61B 5/00
[52] U.S. Cl. .................. 600/584; 600/573; 128/898
[58] Field of Search .................................. 600/573, 584; 128/898

[56] References Cited

U.S. PATENT DOCUMENTS

| | | | |
|---|---|---|---|
| 4,451,251 | 5/1984 | Osterholm | 604/24 |
| 4,910,152 | 3/1990 | Meyers et al. | 436/501 |
| 5,122,515 | 6/1992 | Smith et al. | 514/19 |
| 5,136,019 | 8/1992 | Judd et al. | 530/326 |
| 5,143,084 | 9/1992 | Macemon et al. | 128/771 |
| 5,386,832 | 2/1995 | Wagner et al. | 128/665 |
| 5,542,419 | 8/1996 | Moulton-Barrett et al. | 600/573 |
| 5,654,404 | 8/1997 | Roos et al. | 530/387.3 |
| 5,676,144 | 10/1997 | Schoendorfer | 600/584 |
| 5,703,048 | 12/1997 | Roos et al. | 514/12 |

OTHER PUBLICATIONS

V.R. Young, et. al. Am J. Clin. Nutr. 54:386–94, 1991. "Methionine kinetics and balance at the 1985 FaoWhoUnv intake requirement in adult men . . . ".

K.J. Storch, et al. Am. J. Clin. Nutr. 54:377–85, 1991. "Methionine kinetics in adult men: effects of dietary betain . . . ".

A. Andersson, et al. Clin. Chim. Acta 192:69–76, 1990. "The effect of excess daily methionine intake on plasma . . . ".

Kubota et al., J. Nucl. Med. 32:2118–23, 1991. "Tracer Feasibility for Monitoring Tumor Radiotherapy . . . ".

E. Hayama, et al. Eur. J. Drug Metab. Pharmocokinet 16:287–97. "The kinetics and dynamics of three kinds of radioactive methionine . . . ", 1990.

Blom et al., Hepatology 13:445–54, 1991, Kaye et al., Drugs 340:124–8, 1990. "The Role of Methanethiol in the Pathogenesis of Hepatic Encephalopathy."

Martensson, et al., Scand. J. Gastroentrol. 27–405–11, 1992. "Sulfur Amino Acid Metabolism in Hepatobiliary Disorders."

Gastorenterology vol. 88, p. 1678.

Lauterburg et al., Hepatology 17:418–422, 1993. "Mitochondrial Dysfunction in Alcoholic Patients . . . ".

S. Leskinen–Kallio, et al. Dept. of Oncology and Radiotherapy, Nuclear Medicine and Turku Medical Cyclotron-PET Center, 1991.

*Primary Examiner*—Max Hindenburg
*Assistant Examiner*—Charles Marmor, II
*Attorney, Agent, or Firm*—Jenkens & Gilchrist PC

[57] ABSTRACT

Provided herein is a novel blood test for assessing hepatic function. The test involves administration of a labeled methionine or methionine metabolite to a subject and measurement of the expired label in blood.

22 Claims, 4 Drawing Sheets

$^{13}$C-Methionine Metabolism

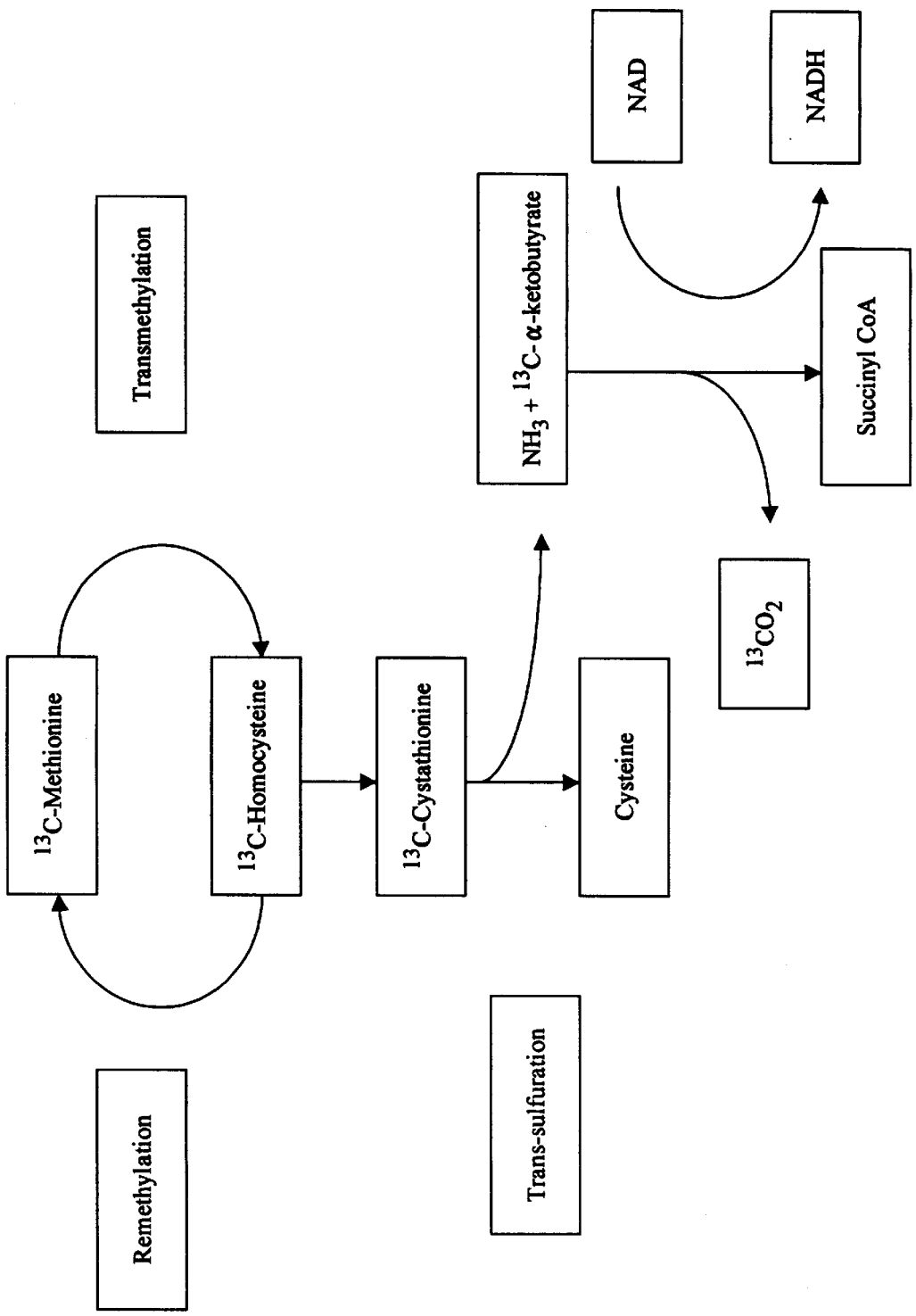
Figure 1: $^{13}$C-Methionine Metabolism

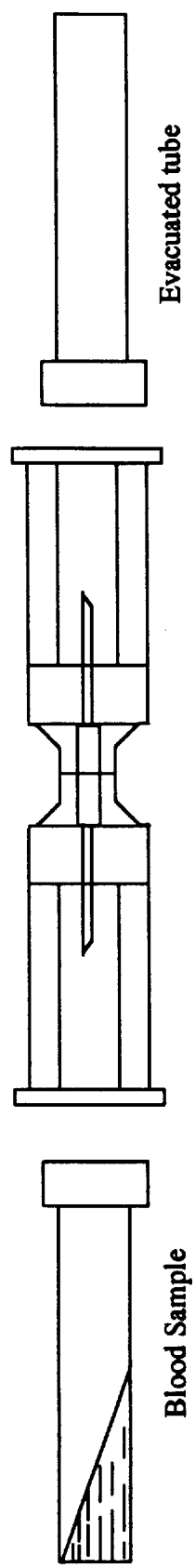
Figure 2: Transfer method for headspace $CO_2$.

Figure 3: Methionine Breath and Blood Results Correlation Plot
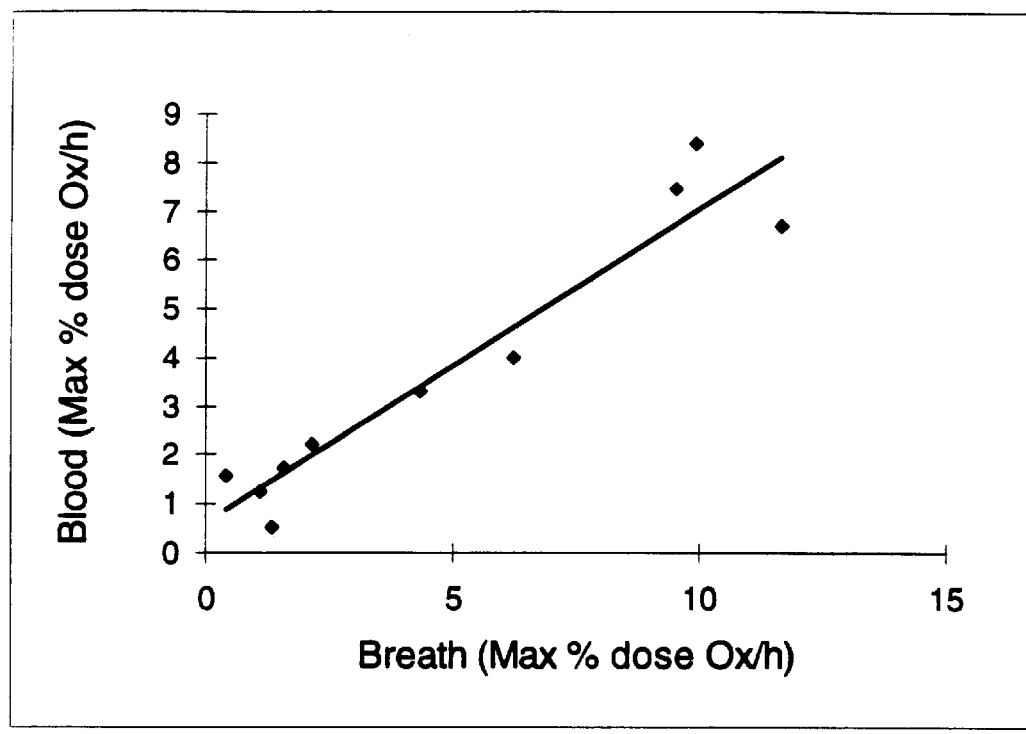

Figure 4: Methionine Blood and Breath Test Diagnostic Thresholds
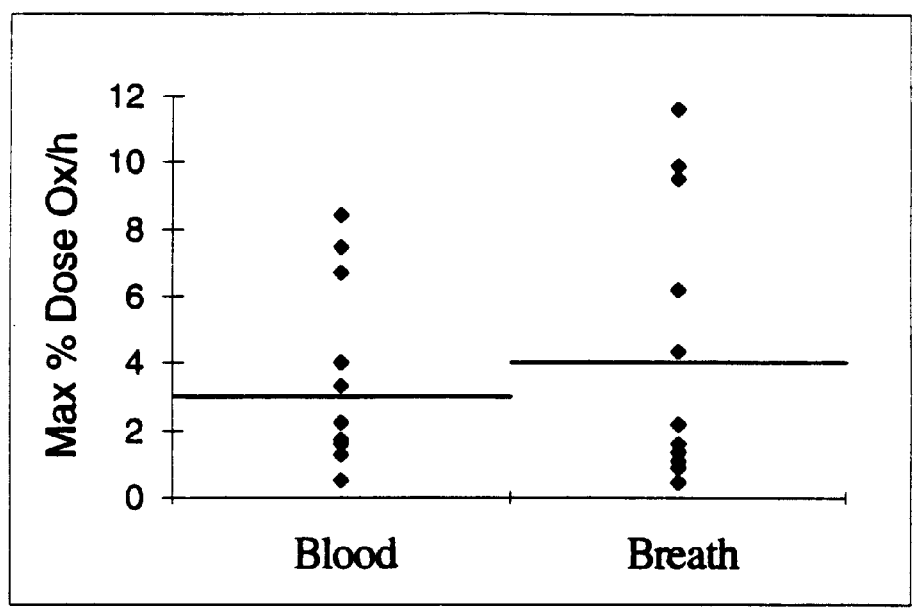

BLOOD TEST FOR ASSESSING HEPATIC FUNCTION

BACKGROUND OF THE INVENTION

1. Field Of The Invention

The present invention relates to a method for monitoring hepatic disease or dysfunction. More specifically, the invention relates to administering labeled methionine or methionine metabolites to an individual and assessing labeled carbon dioxide in blood.

2. Description of the Prior Art

Standard serologic and biochemical serum liver tests have been used to determine the presence of liver disease. However, these tests do not provide an accurate assessment of hepatic functional capacity nor do they detect changes in hepatic disease severity (Gitnick, G. *Surg. Clin. N. Am.* 61:197–207 [1981]). Increasing prothrombin time and decreasing serum albumin concentrations have been used as prognostic indicators of progressive liver disease (Rydning, A., et al. *Scand. J. Gastroenterol.* 25:119–126 [1990]). Significant changes in prothrombin time and albumin may occur in patients for reasons other than liver dysfunction and, at times, only after severe liver decompensation. Further, radiological testing and histological examination of liver biopsies are poor indicators of decreasing hepatic function.

The Child-Pugh (CP) classification is used to determine the degree of liver disease severity. The CP classification reflects the sum of scores derived from clinical and laboratory parameters. Disadvantages of the CP classification include subjective measures (degree of ascites and encephalopathy) and dependence on serum tests (bilirubin, albumin, and prothrombin time) that may be influenced by extrahepatic factors. As a result, the CP classification is a poor measure of patient status and is insensitive to small changes in the patient's condition.

During the last twenty years, much work has been devoted to devising quantitative liver tests. Liver function can be subdivided into three compartments: 1) cytosolic, 2) microsomal, and 3) mitochondrial. Each compartment's function can be evaluated with both quantitative serum and breath tests.

Blood and breath tests have been used for assessing mitochondrial-compartment hepatic function. A typical blood test is the measurement of the arterial ketone body ratio (AKBR). The hepatic mitochondrial redux potential ratio (ratio of NAD/NADH) correlates with the ketone body ratio (acetoacetate/β-hydroxy butyrate) in liver disease. Serial changes in the AKBR can predict hepatic dysfunction, postoperative graft viability, and acute rejection (Asonuma K., S., et al. *Transplantation.* 51:164–171 [1991], Mori K, K., et al. *Ann. Surg.* 211:438–446 [1990]) post liver transplantation. However, recent experiments by Matsushita et al. determined that extrahepatic metabolism of ketone bodies diminishes the value of the AKBR (Matsushita K. et al. *Hepatology.* 20:331–335 [1994]). Additional disadvantages of the AKBR are its labor-intensiveness and the requirement for arterial blood.

Breath tests can also be used to access the mitochondrial compartment hepatic function. The first substrate used as a breath test to measure mitochondrial function was the keto-analog of leucine ketoisocaproic acid (KICA) (Michaletz P. A., et al. *Hepatology.* 10:829–832 [1989]). Decarboxylation of KICA occurs mainly in hepatic mitochondria since anhepatic animals have a 75% reduction in $^{14}CO_2$ production subsequent to administration of $^{14}C$-KICA. Alcohol, which is known to alter the NAD/NADH ratio, deceases KICA decarboxylation. Further experiments with sodium salicylate, an uncoupler of mitochondrial respiration, showed an increase in KICA decarboxylation.

The $^{13}C$ and $^{14}C$-KICA breath tests have been used to access mitochondrial function in controls and in patients with alcoholic and non-alcoholic liver disease (Lauterburg BH, et al. *Hepatology* 17:418–422 [1993]). The KICA breath test showed impaired mitochondrial function in the alcoholic patients compared to controls and non-alcoholic patients. Patients with alcoholic disease had normal aminopyrine breath test and galactose elimination capacity (both measurements of cytosolic function) despite decreased mitochondrial function. These results suggest that KICA decarboxylation reflects hepatic mitochondrial function in patients with chronic alcoholic liver disease.

The $^{13}C$-KICA breath test has also been used to differentiate between alcoholic and nonalcoholic liver-diseased patients (Witschi, A., et al. *Alcohol Clin. Exp. Res.* 18:951–955 [1994], Mion F, et al. *Metabolism.* 44:699–700 [1995]). Lauterburg and co-workers have shown that the $^{13}C$-KICA test can detect mitochondrial changes with the ingestion of the equivalent of two alcoholic drinks or with therapeutic doses of acetylsalicylic acid (ASA, aspirin) (Lauterburg BH, et al. *J. Lab. Clin. Med.* 125:378–383 [1995]). However, the KICA breath test is not widely used. Disadvantages of the KICA breath test are the high cost of the stable isotope and its instability in solution.

These and other disadvantages of the prior art are overcome by the present invention. As shown herein, we provide a novel blood test for assessing hepatic disease or dysfunction.

SUMMARY OF THE INVENTION

The present invention overcomes the limitations of the prior art and provides a method and kit for the assessment of mitochondrial-compartment hepatic function.

Provided herein is a method of assessing hepatic mitochondrial function in a subject comprising the steps of: a) administering to said subject an effective amount of carbon-labeled methionine or carbon-labeled methionine metabolite to said subject; b) collecting blood from said subject; and c) measuring the amount of labeled $CO_2$ in said blood to assess hepatic mitochondrial function in said subject. The label is a carbon label. Preferably the labeled compound administered is $^{13}C$ methionine or $^{13}C$ methionine metabolite, or mixtures thereof. The labeled methionine metabolite is selected from the group consisting of carbon-labeled S-adenosylmethionine, S-adenosylhomocysteine, homocysteine, cystathionine, homoserine and α-ketobutyrate. The carbon-labeled compound may comprise a plurality of labeled carbons.

The method further comprises comparing said amount of labeled carbon with a standard, whereby said comparing yields a measure of hepatic mitochondrial function. The standard comprises the mean isotopic value of $CO_2$ in a control population without hepatic disease or hepatic dysfunction.

The hepatic disease or dysfunction that may be assessed with this method or kit includes liver disease or dysfunction associated with an impairment in the mitochondrial compartment of hepatic tissues. The disease or dysfunction is selected from the group consisting of chronic liver disease, fulminant hepatic failure, viral-induced liver disease, metabolic liver disease, and hepatic dysfunction associated with sepsis or liver trauma.

The label may be measured by techniques commonly used for measuring the presence of labeled species. Isotopic measurement of label is selected from the group consisting of mass spectrometric measurement, laser measurement, infrared detection, nuclear magnetic resonance and liquid scintillation counting of radioactive carbon.

The present invention also provides a kit for assessing hepatic mitochondrial function comprising carbon-labeled methionine or carbon-labeled methionine metabolite in a pharmaceutically acceptable carrier, and a means for collecting blood.

The advantages of the present invention may be gleaned from the following detailed description.

BRIEF DESCRIPTION OF THE DRAWINGS

FIG. 1: Metabolism of Methionine.

FIG. 2: Transfer Method for Headspace $CO_2$.

FIG. 3: Methionine Breath and Blood Results Correlation Plot.

FIG. 4: Methionine Breath and Blood Test Diagnostic Thresholds.

DETAILED DESCRIPTION OF THE INVENTION

Methionine is an essential amino acid which has important roles in various metabolic processes, including protein synthesis (Lehninger, A. L. "Biochemistry." 1977 Worth Publishers, Inc. New York., Storch, K. J., et al. *Am.J. Physiol.* 255:E322–E331 [1988]). $^{13}$C-Methionine is metabolized via a transsulfuration pathway to cystathionine which is subsequently metabolized to alpha-ketobutyrate. Metabolism of alpha-ketobutyrate occurs solely in the hepatic mitochondria with release of $^{13}CO_2$ and reduction of NAD to NADH. These reactions are illustrated in FIG. 1.

Methionine metabolism is impaired in liver disease. Fasting levels of plasma methionine are elevated and the intravenous plasma clearance of methionine is reduced in liver disease when compared to healthy controls (Kinsell, L. W., et al. *Science.* 106:589–590 [1947]; Clowes, G. H. A. J., et al. *Surgery.* 96:675–684 [1984]; Horowitz JH, et al. *Gastroenterology.* 81:668–675 [1981]; Marchesini G, et al. *Hepatology.* 16:149–155 [1992]). Urinary sulfate excretion was also significantly decreased in cirrhotic patients. This suggests that a block in the transsulfuration pathway occurs with liver disease. Methionine plasma clearance was reduced in cirrhotic patients compared with controls. Methionine clearance correlated with the galactose elimination capacity (r=0.82) and with the CP score (r=−0.80). The reduced metabolism of methionine and the decreased formation of methionine end products indicate that mitochondrial function is impaired in cirrhotics.

The present invention features a method of determining hepatic function in a patient using a blood test. This test is sufficiently sensitive to allow detection of not just chronic hepatic conditions where the liver is already irreparably damaged but it also is able to uncover these conditions at an early stage because of its dynamic nature.

The method of the invention commences with a step of administering, preferably orally, a dose of a carbon-labeled methionine to a subject. In an additional embodiment, a carbon-labeled methionine metabolite may be administered to the subject. Useful methionine metabolites include compounds which are transported across the mitochondrial membrane into the mitochondria. Useful metabolites include, but are not limited to metabolites selected from the group consisting of S-adenosylmethionine, S-adenosylhomocysteine, homocysteine, cystathionine, homoserine and α-ketobutyrate, and mixtures thereof. As used herein, the term "compound" refers to labeled methionine or methionine metabolite. Oral administration ensures that the liver, rather than some other organ, gets the first chance to metabolize the labeled compound. The compound is oxidized in the patient forming $^{13}CO_2$ or $^{14}CO_2$ which is subsequently transported to the blood. The blood from the patient is collected and the amount of labeled $CO_2$ in the blood is analyzed. The quantity of labeled $CO_2$ is compared with the standard and this comparison yields a measure of hepatic function. If the compound is administered orally, it preferably is in a pharmaceutically acceptable carrier such as water or a sugar solution but may be delivered chemically bound as a peptide or similar entity and released upon digestion. Alternatively, it may be administered intravenously.

The preferred labeled isotope is a carbon isotope which yields carbon dioxide. The preferred carbon isotopes are $^{13}$C and $^{14}$C. $^{13}$C is more preferred because it is a stable rather than a radioactive isotope.

Methionine or methionine metabolite having an isotope label at the 1-carbon position are preferred. This is because the 1-carbon is excised and eliminated as carbon dioxide at an early step in the oxidative process. However, in an alternative embodiment of the present invention, the compound may have a plurality of carbons labeled. If a $^{13}$C isotope is used, the preferred method of measurement is with a mass spectrometer, but other detection methods can be used, as would be known to one skilled in the art. These include, but are not limited to laser measurement, infrared detection, nuclear magnetic resonance and liquid scintillation counting of radioactive carbon.

The method of the invention can be used to detect hepatic dysfunction and disease by comparing a standard in the form of the mean value of expired isotope in a normal population with value determined from the test subject. This test can be used in identifying the presence of liver dysfunction caused by chronic liver diseases, fulminant hepatic failure, metabolic liver diseases, and liver dysfunction seen in septic or injured patients. For a further and more detailed description of these states, see *Hepatology Textbook of Liver Disease,* Zakim and Bayer, (W. B. Saunders 1990), incorporated by reference herein.

The present invention features a blood test for determining problems in hepatic function. This test is a dynamic rather than a static test and shows hepatic function rather than merely liver cell degradation. The test is relatively inexpensive to carry out and yields rapid results. While radioactive isotopes can be used in the test, it preferably is carried out with stable isotopes.

In the preferred embodiment, the individual is first required to fast overnight. This minimizes metabolic effects of meal absorption and the contribution of endogenous label appearing in the blood from natural levels of the endogenous isotope in the diet. However, the test may be conducted without requiring overnight fasting. Preferably at least two baseline blood samples are collected and the mean isotope value in these samples is used as a background. In an alternative embodiment, only one background measurement is made or, alternatively, no background measurement is made. If no background measurement is made, the amount of label in the blood is taken as the measurement for comparison with a control value. If a background measurement is made, this background is subtracted from the labeled carbon levels determined following isotopic administration in order to obtain the change in labeled species level.

If the compound is administered orally, it is preferable to wait a sufficient amount of time after administration before collecting the blood sample(s) to allow metabolism of the labeled compound to release the labeled species. A sufficient amount of time is about 5 minutes to about 120 minutes, preferably about 10 minutes to about 90 minutes, and most preferably about 30 minutes to about 60 minutes. If the compound is administered intravenously, the sufficient amount of time is about 5 minutes to about 120 minutes, preferably about 10 minutes to about 90 minutes, and most preferably about 30 minutes to about 60 minutes. If the compound is an amino acid or methionine metabolite with a chiral center, it is preferably the L-stereoisomer, but may also be the D-stereoisomer or a racemic mixture thereof.

All blood samples, both those collected prior to administration of the isotope and those after administration, may be collected with a commercially available blood collection device such as, but not limited to, a heparinized Vacutainer "butterfly" blood collection set (Vacutainer, Franklin Lakes, N.J.), a syringe, or a Vacutainer holder with an evacuated Vacutainer tube. Preferably, the blood specimen is venous blood, but arterial and/or capillary blood can also be tested. The blood sample is then reacted with acid to liberate dissolved $CO_2$. Suitable acids include, but are not limited to, citric, phosphoric, hydrochloric and sulfuric acid. Preferably, the acid is citric acid. The ratio of saturated citric acid to specimen is preferably 0.01 to 0.5 (volume/volume), and most preferably 0.03 to 0.1 (volume/volume). The amount and type of acid to be added to the specimen can be determined by one of skill in the art. Addition of acid to the specimen is needed to generate a suitable headspace specimen having $CO_2$ for analysis. The headspace containing the labeled $CO_2$ is either sampled directly or transferred to an evacuated Exetainer tube (Labco Ltd, U.K.) or Vacutainer tube prior to analysis.

The following examples serve to illustrate specific embodiments of the invention, but should not be considered as a limitation on the scope of the invention.

EXAMPLE 1
Administration of the Test

A pre-measured 100 mg dose of L-1-$^{13}$C-methionine (MassTracer, Woburn, Mass.) was solubilized in 20 ml sterile water and administered orally. The cup was immediately filled with an additional 150–200 ml of water and consumed by the patient. Following the administration of the dose, blood samples were collected at 40 minutes. After the blood was collected, $CO_2$ was liberated from the sample and transferred to an evacuated Exetainer breath storage tube. The amount of $^{13}CO_2$ in the storage tube was measured with a Europa Scientific 20/20 gas isotope ratio mass spectrometer (Europa Scientific, Cincinnati, Ohio). The ratio of $^{13}CO_2$ to $^{12}CO_2$ (mass 45 to 44) is measured in the sample and compared to a reference gas (5% $CO_2$, balance 75% $N_2$, 20% $O_2$). The reference gas had been calibrated against international standards. The units of measurement were atom % $^{13}$C and defined by:

Atom % $^{13}C = {}^{13}CO_2/({}^{13}CO_2 + {}^{12}CO_2) \times 100\%$ $CO_2$ standards at three different enrichments, covering a range similar to that produced by a typical breath test, were run before and after each daily run to check instrument performance. The analytical precision of the instrument was 0.0001 atom % $^{13}$C.

The atom percent excess (APE) $^{13}$C value for the 40 minute sample was converted to a value determined for a one hour period. We used the 40 minute enrichment (APE) to determine a maximum percent dose oxidized per hour (max % oxidation/h) Schneider, J. F., et al. *Clin. Chim. Acta.* 84:153–162 [1978]). The quantity of $^{13}$C exhaled was estimated by assuming $CO_2$ production is 5 mmol/min/m² body surface area (Schneider, J. F., et al. *Clin. Chim. Acta.* 84:153–162 [1978]). The maximum percent dose metabolized was calculated as:

Max % dose/hour=[(BSA(m²)×(APE$_{max}$/100)×5 mmol/min/m²]/0.65 mmol×6

Where BSA was the body surface area, APE$_{max}$ was the maximum atom percent excess for a ten minute interval, 0.65 mmol was the quantity of $^{13}$C-labeled methionine administered and the constant 6 converts the 10 minute interval to one hour.

50 µl of saturated citric acid solution was added by syringe to each 3 ml Vacutainer blood sample. The sample was mixed well for 15 seconds by Vortex mixer. The carbon dioxide headspace gas was transferred to a 10 ml Vacutainer tube using a double-sided needle gas transfer device as illustrated in FIG. 2. The gas transfer device was constructed out of standard Vacutainer™ blood tube holders, an adapter and blood collection needles as shown below. Each Vacutainer blood tube holder contained a needle (22 gauge) which pierced the evacuated tubes.

The analyst pierced the blood sample and new evacuated blood tube simultaneously which caused headspace gas to transfer into the evacuated tube. The tube with newly transferred $CO_2$ gas was removed first from the tube holder. This transferred gas tube was analyzed by a Gas Isotope Ratio Mass Spectrometer.

EXAMPLE 2
Accuracy and Precision

An experiment was conducted to determine the accuracy and precision of the transfer technique. Six sodium bicarbonate standards of varying concentration of $^{13}$C were added to an evacuated tube. Ten replicates of each bicarbonate standard were treated with a saturated citric acid solution (50 µl) to lower pI-I and release $CO_2$ into the headspace of the evacuated tube. Five of the replicates were transferred using the above described device. The mean of the atom per cent $^{13}$C (ratio of $^{13}$C to sum of $^{12}$C and $^{13}$C times 100), standard deviation (SD) and coefficient of variation (CV) for each bicarbonate standard is shown below:

TABLE 1

Accuracy and Precision of Standard Preparation

| Standard/Statistics | Atom % C13 Without Transfer | Atom % C13 With Transfer |
| --- | --- | --- |
| Std 1 mean | 1.08631 | 1.08623 |
| Std 1 SD | 0.00013 | 0.00017 |
| Std 1 CV | 0.012% | 0.016% |
| Std 2 mean | 1.09412 | 1.09413 |
| Std 2 SD | 0.00020 | 0.00014 |
| Std 2 CV | 0.018% | 0.013% |
| Std 3 mean | 1.09750 | 1.09745 |
| Std 3 SD | 0.00008 | 0.00024 |
| Std 3 CV | 0.007% | 0.021% |
| Std 4 mean | 1.10324 | 1.10322 |
| Std 4 SD | 0.00013 | 0.00030 |
| Std 4 CV | 0.012% | 0.027% |
| Std 5 mean | 1.11036 | 1.11044 |
| Std 5 SD | .00057 | .00054 |
| Std 5 CV | 0.051% | 0.049% |
| Std 6 mean | 1.14009 | 1.13996 |
| Std 6 SD | .00047 | .00060 |
| Std 6 CV | 0.041% | 0.053% |

There was no statistical difference (paired t-test, p>0.05) between the standards with or without transfer of headspace gas. These results demonstrated that the transfer technique would provide accurate results and eliminate potential needle clogging problems. The transfer technique would allow automated measurements in commercial instruments that are set-up to analyze gas samples in evacuated blood tubes.

EXAMPLE 3
Volume of blood required for analysis

The volume of blood required for accurate $^{13}CO_2$ analysis was investigated with ten blood samples which were transferred by syringe into 1 and 2 ml aliquots. Blood samples were transferred into an evacuated tube, 50 µl saturated citric acid added, and the resulting headspace gas was transferred to another evacuated tube. The percentage of carbon dioxide gas for each sample is shown below in Table 2.

TABLE 2

Percent CO2 derived from 1 and 2 ml aliquots of blood.

| Sample No. | % $CO_2$ 1 ml aliquot | % $CO_2$ 2 ml aliquot |
|---|---|---|
| 1 | 1.51 | 2.69 |
| 2 | 1.66 | 2.71 |
| 3 | 1.56 | 2.29 |
| 4 | 2.58 | 3.81 |
| 5 | 2.47 | 3.77 |
| 6 | 2.41 | 3.91 |
| 7 | 2.28 | 3.84 |
| 8 | 2.45 | 3.58 |
| 9 | 2.31 | 3.77 |
| 10 | 2.58 | 3.81 |

The gas isotope ratio mass spectrometer was linear between 1 and 5% $CO_2$. However, the best accuracy was obtained between 2 and 5% $CO_2$. It was decided that a two ml aliquot would eliminate analytical problems for those samples of low $CO_2$ gas (less than 100% transfer of gas). The two ml aliquot would insure greater than 2% $CO_2$ for each sample. This has been verified in more than 80 methionine tests.

EXAMPLE 4
Requirement for liberation of dissolved bicarbonate in blood

We investigated whether lowering the pH, by adding citric acid, was required for the analysis. Carbon dioxide exists in blood as either bicarbonate or dissolved gaseous carbon dioxide. If blood is injected into an evacuated tube, some of the dissolved carbon dioxide gas in blood transfers into the headspace of the tube. It was not known whether the natural transfer of carbon dioxide into the headspace represented an equivalent isotopic ratio to the dissolved bicarbonate in blood.

Ten blood samples with varying $^{13}CO_2$ levels were prepared with and without adding 50 µl saturated citric acid. The headspace gas of all samples were transferred into new evacuated tubes. The delta per mil C13 values for each replicate sample prepared both ways is shown in Table 3.

TABLE 3

Effect of pH on $^{13}CO_2$ Recovery.

| No Citric Acid Added | | With Citric Acid Added | |
|---|---|---|---|
| % $CO_2$ | Delta C13 per mil | % $CO_2$ | Delta C13 per mil |
| 1.13 | −23.16 | 2.57 | −21.40 |
| 1.58 | −20.23 | 2.86 | −19.86 |
| 1.80 | −4.13 | 2.55 | −3.88 |
| 2.76 | −8.16 | 2.84 | −3.69 |
| 1.30 | −22.61 | 2.73 | −21.23 |
| 1.14 | −8.38 | 2.78 | −7.36 |

TABLE 3-continued

Effect of pH on $^{13}CO_2$ Recovery.

| No Citric Acid Added | | With Citric Acid Added | |
|---|---|---|---|
| % $CO_2$ | Delta C13 per mil | % $CO_2$ | Delta C13 per mil |
| 0.99 | −4.89 | 2.05 | −4.42 |
| 1.06 | −20.67 | 2.08 | −18.90 |
| 1.01 | −15.13 | 2.17 | −11.96 |

The citric acid treated blood samples were significantly higher (paired t test, p<0.05) in $^{13}C$ levels as well as percent $CO_2$ gas. Since the $^{13}C$ values are higher with the citric acid treatment, this suggests that the headspace gas in the non-citric acid treated tubes were not at isotopic equilibrium. The vacuum in the evacuated tubes is not sufficient to extract carbon dioxide as dissolved bicarbonate, but merely as dissolved gaseous carbon dioxide. Therefore, acid treatment is required to obtain a total $^{13}C$ level.

EXAMPLE 5
Requirement for refrigeration of blood samples

Blood collection samples which do not require refrigeration offer a marketing advantage for the product. We investigated whether blood samples that were stored at room temperature would show similar $^{13}C$ results to samples stored and shipped frozen.

Blood samples (6 ml) were collected from volunteers. Samples were immediately aliquoted (2 ml) by syringe into new blood tubes. One aliquot was kept at room temperature and the other aliquot was immediately frozen (−20° C.). The frozen aliquot was shipped on dry ice and stored frozen until analysis. Both types of samples were analyzed as outlined above. The atom % C13 of both sample treatments are shown in Table 4.

TABLE 4

Effect of Sample Storage Temperature.

| Patient No. | Stored at Room Temp Atom % C13 | Stored Frozen Atom % C13 |
|---|---|---|
| 1 | 1.10064 | 1.08510 |
| 1 | 1.10048 | 1.10135 |
| 2 | 1.09534 | 1.09448 |
| 2 | 1.09613 | 1.09713 |
| 3 | 1.09901 | 1.09892 |
| 3 | 1.09936 | 1.09877 |
| 4 | 1.09906 | 1.08784 |
| 4 | 1.09933 | 1.09348 |

Samples stored frozen showed more variability compared to samples stored at room temperature. We attribute the variability with the frozen sample to the generation of a breakdown product which either interferes with the analysis or contributes $^{12}C$. The data shows that samples kept at room temperature have reproducible results. In addition, we investigated whether samples at room temperature degraded over time. There was no significant change in the $^{13}C$ level for samples analyzed up to 4 weeks later (data not shown). These experiments indicated that samples could be stored and transported at room temperature before analysis.

Example 6
Comparison of the Methionine Breath Test with the Methionine Blood Test Carbon dioxide, the end product of cellular respiration, is transported to the lungs by the circulating blood. Thus, respiratory $CO_2$ can either be sampled in the exhaled breath or liberated from blood. Blood collection is considered a non-invasive procedure by the medical community and represents a viable way to obtain a $CO_2$ sample. In light of this, we conducted several studies to investigate the relationship between blood and breath collection for determining results of the MBT.

The objective of this example was to provide a direct comparison of results obtained with the Methionine Blood and Breath tests. Several volunteers representing a broad range of liver function were given $^{13}C$-Methionine prior to simultaneous collection of blood and breath. Five volunteers had healthy livers while the remaining six were shown to be at various stages of liver dysfunction using the Childs-Pugh classification system. A summary of the results are given in Table 5.

TABLE 5

Methionine Breath and Blood Test Results

| Participant | Liver Status | Breath* | Blood* | Difference* |
|---|---|---|---|---|
| 1 | Healthy Volunteer | 9.91 | 8.41 | 1.50 |
| 2 | Healthy Volunteer | 4.32 | 3.32 | 1.00 |
| 3 | Healthy Volunteer | 11.65 | 6.71 | 4.94 |
| 4 | Healthy Volunteer | 9.51 | 7.45 | 2.06 |
| 5 | Healthy Volunteer | 6.20 | 4.00 | 2.20 |
| 6 | B-7 | 1.08 | 1.26 | −0.18 |
| 7 | B-7 | 1.57 | 1.74 | −0.17 |
| 8 | B-8 | 1.33 | 0.51 | 0.82 |
| 9 | B-9 | 2.15 | 2.22 | −0.07 |
| 10 | C-10 | 0.91 | ** | |
| 11 | C-11 | 0.42 | 1.58 | −1.16 |
| Mean | | 4.46 | 3.72 | 1.09 |
| SD | | 4.17 | 2.83 | 1.73 |

*-Results expressed as maximum percent methionine oxidized per hour.
**-Methionine Blood Test not performed.

Data analysis revealed an excellent correlation (r=0.95) for the breath/blood comparison. A plot of the results is given in FIG. 3.

FIG. 4 presents a comparison of the diagnostic threshold values for the $^{13}CO_2$ measured in the blood and breath. The threshold established for the blood-derived $^{13}CO_2$ was one unit lower, as expressed as maximum percent methionine oxidized per hour, than for breath. This difference in the $^{13}CO_2$ values derived from blood and breath is confirmed by the mean difference of 1.09 calculated in table 5. This suggests a temporal shift in $^{13}CO_2$ values for breath and blood sampled simultaneously. This feature has little influence on the diagnostic ability of the test as long as the relationship is consistent. In this population the diagnostic threshold of 3 (max. % met. Ox./h) for blood derived $^{13}CO_2$ is comparable to the breath threshold of 4 (max. % met. Ox./h). A plot of the data is given in FIG. 4.

Many other variations and modifications may be made in the methods herein described, by those having experience in this art, without departing from the concept of the present invention. Accordingly, it should be clearly understood that the methods described in the foregoing description are illustrative only, and not intended as a limitation on the scope of the invention.

What is claimed is:

1. A method of assessing hepatic mitochondrial function in a subject comprising the steps of:
 a) administering to said subject an effective amount of carbon-labeled methionine or methionine metabolite to said subject;
 b) collecting a blood specimen from said subject; and
 c) measuring the amount of labeled carbon in said blood specimen to assess hepatic mitochondrial function in said subject.

2. The method according to claim 1 wherein said carbon-labeled methionine or methionine metabolite is selected from the group consisting of $^{14}C$ methionine or methionine metabolite and $^{13}C$ methionine or methionine metabolite, or mixtures thereof.

3. The method according to claim 1 wherein said carbon-labeled methionine is $^{13}C$ methionine.

4. The method according to claim 1 wherein said carbon-labeled methionine or methionine metabolite is labeled at the 1-position of methionine or the 1-position of the methionine metabolite.

5. The method of claim 1 wherein said carbon-labeled methionine or methionine metabolite comprises a plurality of labeled carbons.

6. The method according to claim 1 wherein said labeled carbon in said blood is labeled carbon dioxide.

7. The method according to claim 6 wherein said labeled carbon dioxide is $^{13}C$ carbon dioxide.

8. The method according to claim 1 wherein said administering step comprises administering carbon-labeled methionine or methionine metabolite in a pharmaceutically acceptable carrier.

9. The method according to claim 1 further comprising comparing said amount of expired labeled carbon with a standard, whereby said comparing yields a measure of hepatic mitochondrial function.

10. The method according to claim 9 wherein said standard comprises the mean value of expired label in a control population without hepatic disease or hepatic dysfunction.

11. The method according to claim 1 or claim 9 wherein said assessing mitochondrial function is used to diagnose hepatic disease or hepatic dysfunction.

12. The method according to claim 11 wherein said hepatic disease or dysfunction is selected from the group consisting of chronic liver disease, fulminant hepatic failure, viral-induced liver disease, metabolic liver disease, and hepatic dysfunction associated with sepsis or liver trauma.

13. The method according to claim 1 wherein said measuring comprises isotopic measurement of labeled carbon.

14. The method according to claim 13 wherein said measurement is selected from the group consisting of mass spectrometric measurement, laser measurement, infrared detection, nuclear magnetic resonance and liquid scintillation counting of radioactive carbon.

15. The method according to claim 1 wherein said blood specimen is selected from the group consisting of venous, capillary and arterial blood.

16. The method according to claim 15 wherein said blood specimen is treated with an acid prior to analysis of $CO_2$.

17. The method according to claim 16 wherein said acid is citric acid.

18. The method of claim 1 wherein said carbon-labeled methionine metabolite is selected from the group consisting of carbon-labeled S-adenosylmethionine, S-adenosylhomocysteine, homocysteine, cystathionine, homoserine and α-ketobutyrate.

19. A kit for assessing hepatic mitochondrial function comprising carbon-labeled methionine or methionine metabolite in a pharmaceutically acceptable carrier.

20. The kit of claim 19 further comprising a means for collecting blood.

21. The kit of claim 20 wherein said means for collecting blood is a Vacutainer tube and an acid.

22. The kit of claim 21 wherein said acid is citric acid.

* * * * *